(12) United States Patent
Wu

(10) Patent No.: US 8,871,473 B2
(45) Date of Patent: Oct. 28, 2014

(54) METHOD FOR PRODUCING γ-CYCLODEXTRIN BY SIMULTANEOUS USE OF γ-CYCLODEXTRIN GLYCOSYLTRANSFERASE AND ISOAMYLASE

(71) Applicant: Jiangnan University, Wuxi (CN)

(72) Inventor: Jing Wu, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 13/925,837

(22) Filed: Jun. 25, 2013

(65) Prior Publication Data

US 2014/0199733 A1   Jul. 17, 2014

(30) Foreign Application Priority Data

Jan. 17, 2013 (CN) .............................. 20130036791

(51) Int. Cl.
*C12P 19/18* (2006.01)

(52) U.S. Cl.
USPC .................. 435/97; 435/98; 127/40; 536/103

(58) Field of Classification Search
USPC .......................... 435/97, 98; 127/40; 536/103
See application file for complete search history.

(56) References Cited

U.S. PATENT DOCUMENTS 4,970,164 A * 11/1990 Yang et al. ..................... 435/280
6,235,505 B1 * 5/2001 Grull et al. ...................... 435/98

OTHER PUBLICATIONS

Duan X. et al. Enhancing the Cyclodextrin Production by Synchronous Utilization of Isoamylase and gamma CGTase. Applied Microbiol Biotechnol Jul. 26, 2012. 97(8)3467-74.*
Nakagawa Y. et al. Site Directed Mutations in Alanine 223 and Glycine 255 . . . J Biochem 140:329-336, 2006.*
van der Veen B. et al. Engineering of Cyclodextrin Glycosyltransferase Reaction and Product Specificity. Biochimica et Biophysica Acta 1543:336-360, 2000.*
Wang L. et al. Enhanced Production of gamma Cyclodextrin by Optimization of Reaction . . . Food Chemistry 141:3072-76, 2013.*
Li Z. et al. Gamma Cyclodextrin: A Review on Enzymatic Production and Applications. Applied Microbiol Biotechnol 77:245-255, 2007.*
Rendleman J. Enhancement of Cyclodextrin Production Through Use of Debranching Enzymes Biotechnology Applied Biochem 26:51-61, 1997.*

* cited by examiner

*Primary Examiner* — Ralph Gitomer
(74) *Attorney, Agent, or Firm* — Lili Chen

(57) ABSTRACT

The present invention provides a method for the production of γ-CD, comprising making a starch slurry, incubating with γ-CGTase and isoamylase simultaneously for γ-CD production, forming a complex of γ-CD and an organic complexant, and purifying γ-CD from the complexant. The present invention provides a simple and cost-effective method for producing high purity γ-CD, which has a short production cycle, a high conversion rate, and is adaptable to large-scale industrial production.

4 Claims, No Drawings

METHOD FOR PRODUCING γ-CYCLODEXTRIN BY SIMULTANEOUS USE OF γ-CYCLODEXTRIN GLYCOSYLTRANSFERASE AND ISOAMYLASE

CROSS-REFERENCES AND RELATED APPLICATIONS

This application claims priority of Chinese Application No. CN 201310036791.9, entitled "A Method for Producing gamma-Cyclodextrin by Simultaneous Use of gamma-Cyclodextrin Glycosyltransferase and Isoamylase", filed Jan. 17, 2013, which is herein incorporated by reference in its entirety.

BACKGROUND OF THE INVENTION

1. Field of the Invention

The present invention relates to a method for γ-cyclodextrin production, and more particularly relates to a method of producing γ-cyclodextrin by using γ-cyclodextrin glycosyltransferase and isoamylase simultaneously.

2. Description of the Related Art

Cyclodextrins (CDs) are a group of structurally related natural products produced from starch or starch derivatives by catalytic action of cyclodextrin glycosyltransferase (CGTase; EC 2.4.1.19). CDs are composed of D-glucopyranose units linked by a α-1,4-glycosidic bond. The most extensively studied and exploited CDs are α-CD, β-CD and γ-CD, which are composed of 6, 7 and 8 α-1, 4 linked glucose units, respectively. The unique structure of CDs makes it easy for CDs to embed organic and inorganic compounds. Therefore, CDs are widely used in the field of food, chemistry industry, medicine, agriculture, biotechnology and textile technology. Among the three CDs, β-CD has a limited solubility in water, which allows β-CD to be easy obtained by fractional crystallization. However, the low solubility in water restricts its application as embedding compounds. Though α-CD has larger solubility in water, it is not easy to produce on industrial scale because of the low yield and costly purification. γ-CD has bigger capacity and larger solubility, which enable it to form complexes with lager molecules and improve the solubility and emulsification characteristic of the substance. At the same time, because γ-CD is safe and bland, it is possible for γ-CD to be applied in food products and medicine. Unfortunately, due to the low yield and high purification cost, the production of γ-CD can not satisfy the market needs. Only a few companies, such as Wacker and Cyclolab, produce γ-CD in a small scale. To date, γ-CD is produced from starch by amylase and γ-cyclodextrin glycosyltransferase (γ-CGTase) digestion. The starch raw material contains more than 75-85% amylopectin, which means there is one α-1,6-glycosidic bond every 17-28 glucose units. Because the γ-CGTase can not hydrolyze the α-1,6-glycosidic bond, the γ-CD yield is very low and the production cycle is very long.

Isoamylase (EC 3.2.1.68) which is mainly used for food additives is a hydrolase that catalyzes the hydrolysis of α-1,6-glycosidic branch linkages in glycogen and amylopectin. During CDs production, isoamylase can be added to hydrolyze the α-1,6-linkages, and then, the CGTase carry out the cyclization reaction. Therefore, methods of using isoamylase and CGTase were developed to improve the yield and lower the cost of CDs production. Ivan Pishtiyski (Pishtiyski, I. and B. Zhekova (2006). "Effect of different substrates and their preliminary treatment on cyclodextrin production." World Journal of Microbiology and Biotechnology 22(2): 109-114) achieved 65% yield of CDs using 2.5% potato starch as substrate and a two-step conversion reaction using pullulanase for debranching and CGTase for cyclization. Rendleman (Rendleman, J. A. Jr. (1997). "Enhancement of cyclodextrin production through use of debranching enzymes." Biotechnology and applied biochemistry 26(1): 51-61.) achieved 76% yield with 10% waxy corn starch as substrate by using debranching enzyme (pullulanase and isoamylase) and α-CGTase for cyclization at 15° C. However, the concentration of the substrate was too low and the reaction time took as long as 5 days. Isoamylase is almost inactivated under alkalic condition and wild-type γ-CGTase only has 10% relative activity under neutral pH. As a result, there is no report of using isoamylase and γ-CGTase simultaneously for γ-CD production. The relative activity of a γ-CGTase mutant, γ-CGTase (A223K) from Alkalophilic Bacillus 7364 (Nakagawa Y, Takada M, Ogawa K, Hatada Y, Horikoshi K. "Site-directed mutations in Alanine 223 and Glycine 255 in the acceptor site of gamma-Cyclodextrin glucanotransferase from Alkalophilic Bacillus clarkii 7364 affect cyclodextrin production." J. Biochem. 2006 140(3):329-36.), has more than 3-fold increase under neutral pH (pH 7.5) when compared to that of the wild type enzyme, which makes it possible to use isoamylase and γ-CGTase (A223K) simultaneously for γ-CD production. The present invention provides a method for producing γ-CD in one-step conversion reaction using isoamylase and γ-CGTase (A223K) under a neutral pH.

DETAILED DESCRIPTION

The present invention provides a simple and cost-effective approach for γ-CD production by using isoamylase and γ-CGTase simultaneously.

The method comprises the following steps:

1. Production of γ-CGTase (A223K) by E. coli BL21 (DE3)/pET24a(+)-γ-CGTase (A223K)

The gene of γ-CGTase (A223K) from Alkalophilic Bacillus 7364, wherein the Alanine residue at the position 223 of the wild type enzyme is changed to Lysine, was cloned into a pET24a(+) plasmid and the plasmid was transfected into E. coli BL21(DE3) following standard molecular cloning procedures. The recombinant E. coli BL21(DE3)/pET24a(+)-γ-CGTase (A223K) was cultured to produce γ-CGTase (A223K). To get the crude enzyme, the supernatant was separated from the culture by centrifugation at 8000 g for 10 min at 4° C. The γ-CGTase used herein, unless otherwise noted, refers to γ-CGTase (A223K) from Alkalophilic Bacillus 7364.

2. Production of γ-CD

The starch was suspended in water to a final concentration of 5-20% and heated to 60-90° C. for about 5-15 min in order to be gelatinized under constantly stirring. Then, 10-100 U γ-CGTase and 10-100 U isoamylase per gram of starch were added to the starch slurry after the suspension was cooled down to 40-60° C. and the pH was adjusted to 7.0-8.0. After that, 5% (w/v) organic agent was added and the slurry was kept for 6-12 h. At last, the organic agent was removed and the complexant-free aqueous solution was crystallized into γ-CD.

The method of culturing the recombinant E. coli BL21 (DE3)/pET24a(+)-γ-CGTase (A223K) for γ-CGTase (A223K) production is described in the publication by Ji et al. (Ji, Li-ping; Wu, Dan; Wu, Jing; Chen, Jian. Optimization of fermentation in shake flasks for recombinant γ-CGTase expression in E. coli. China Biotechnology, 2011, 31(10):50-56).

The isoamylase used here was produced by our lab and the procedure to prepare isoamylase has been described in the published Chinese patent application (Application number: 201110459137.x).

The γ-CD was analyzed by HPLC. The supernatant of complexant-free aqueous solution was obtained after centrifugation at 8000 r/min for 15 min. 0.45 μL α-amylase was added to the supernatant. One hour later, the supernatant was filtered through a 0.45 μm filter (Whatman) ahead of being injected into HPLC system (Waters 600) for analysis. Then, 10 μL filtrate was used for analysis and the concentration of γ-CD was determined through HPLC by using a ZORBAX $NH_2$ column (4.6 mm×150 mm) at 40° C. The mobile phase consisted of 75% acetonitrile and 25% water with a flow rate of 1 mL/min. The eluted was detected by a RI detector (Waters2410).

The organic agent used as complexant was cyclododecanone which is cheap and can be easily removed from reaction mixtures by azeotropic distillation due to the low boiling point of cyclododecanone.

The method of removing organic agent to get γ-CD was as follows:

1) When the catalytic reaction was over, the mixture was firstly heated to inactivate the enzymes and then filtered directly. The filtered cake was washed with water for 2-3 times.
2) The filtered cake which contained starch, a complex formed by organic agent and γ-CD was collected and dissolved in water.
3) The organic agent was removed by azeotropic distillation, and then the complexant-free aqueous solution containing free γ-CD was filtered by Buchner funnel to get rid of insoluble starch.
4) The γ-CD solution was concentrated with a rotary evaporator and then crystallized into pure γ-CD at a low temperature.

The technical principles of the present invention are as follows:

In addition to catalyze cyclization reactions to produce γ-CD from starch, γ-CGTase can also catalyze coupling, disproportionation and hydrolysis reactions. Coupling reaction is a reverse reaction of cyclization. When using maltooligosaccharide as a substrate to produce γ-CD, small molecules such as glucose in the substrate may inhibit the cyclization reaction and lower the final yield. The present invention uses gelatinized starch as the substrate to produce γ-CD, which eliminates the inhibition of the cyclization reaction caused by small sugar molecules. Gelatinized starch is generated by stirring granular starch under warm temperatures and making it become fully swollen. However, the starch containing a large number of α-1, 6 glycosidic bonds, which can not be hydrolyzed by γ-CGTase. Using γ-CGTase alone can not make a full use of the starch sustrate. Isoamylase can hydrolyze α-1, 6 glycosidic bond. Combining isoamylase with γ-CGTase can facilitate the cyclization reaction, shorten the reaction time, and increase γ-CD conversion rate. The cyclization reaction is a reversible reaction. To move the reaction to the direction of γ-CD production and increase conversion, γ-CD needs to be continuously removed from the reaction system. Removal of γ-CD is achieved by adding organic solvent that can form water insoluble complex with γ-CD in the reaction system. During the cyclization reaction, γ-CD forms water insoluble complex with the organic solvent and is removed from the aqueous reaction system.

The present invention provides a method for the production of γ-CD based on the characteristics of the γ-CGTase (A223K) and isoamylase as well as the property of γ-CD.

Comparing to currently available technologies, the present invention has the following advantages:

1) the method has a high conversion rate, and is cost-effective and easy to adapt to the large-scale production.
2) the total reaction time is shortened to 6-12 hours, compared to five days of that of other technologies.
3) the temperature for the conversion reaction is relatively low, and therefore the method does not require drastic temperature changes, consumes less energy, and is suitable for industrial production.
4) The method directly uses starch as a substrate, eliminating the inhibition of the reaction for producing γ-cyclodextrin caused by small sugar molecules like glucose.
5) Adding a certain proportion of organic solvent to form a complex with γ-CD can continuously remove γ-CD from the reaction system, moving the reaction towards to the direction of generating more γ-CD and thus increasing the conversion rate. The total conversion rate reached about 70%, wherein the ratio of the γ-CD and β-CD is about 9:1.
6) The process to remove organic solvent is relatively simple, and high purity (up to 95%) of the product can be obtained. In addition, residual organic solvents can be used in the pharmaceutical industry.

The present invention provides a simple and cost-effective method for producing high purity γ-CD from starch, which has a short production cycle, a high conversion rate, and is adaptable to large-scale industrial production.

EXAMPLES

The following examples were provided by way of illustration only, and not by way of limitation. Standard experimental operations not specifically described in the specification were preformed according to standard molecular cloning protocols described in "Molecular Cloning: A Laboratory Manual" (by Sambrook J and Russell D, Cold Spring Harbor Laboratory Press, 2001).

The EZ-10 Spin Column Plasmid Mini-Pre ps kit, agarose gel DNA purification kit were purchased from Tiangen Biotech CO., LTD (Beijing, China). DNA sequencing was performed by Shanghai Sangon Biological Engineering Technology & Services Co. Ltd. (Shanghai, China). Tryptone and yeast extract were obtained from Oxoid (Hampshire, UK). Isopropyl β-D-1-thiogalactopyranoside (IPTG) and the standard samples of γ-CD were purchased from Sigma (Shanghai, China). Acetonitrile was purchased from Honeywell, USA. Unless otherwise noted, other reagents including corn starch were analytically pure and obtained from SCRC (Sinopharm Chemical Reagent Co. Ltd. (Shanghai, China)).

Example 1

Construction of Recombinant Plasmid for Expression of γ-CGTase (A223K)

According to the gene sequence of γ-CGTase from Alkalophilic *Bacillus* 7364, the γ-CGTase (A223K) mutant gene was synthesized through PCR with special designed primers. The gene fragment was ligated into pET24a to construct the recombinant vector, which was transformed into *E. coli* JM109 for amplification at 37° C. for 8 h with Luria-Bertani containing kanamycin. The recombinant vector pET24a(+)-γ-CGTase (A223K) was identified by restriction analysis and then transformed into *E. coli* BL21 (DE3) to get recombinant *E. coli* BL21(DE3)/pET24a(+)-γ-CGTase (A223K) for expression of γ-CGTase (A223K). The recombinant *E. coli* BL21(DE3)/pET24a(+)-γ-CGTase (A223K) was cultivated on TB medium for 24-48 hours and the supernatant, which was derived from separating the cells by centrifugation at 8000 g, 4° C., for 10 minutes, was used as crude enzyme. The enzyme was precipitated from the supernatant solution by 50% (w/v) ammonium sulfate and then the precipitant was dialyzed against Gly-NaOH (pH 10.0, 50 mM) buffer overnight. The cyclization activity of the concentrated enzyme can reach 50.5 U per milliliter.

Example 2

Production of γ-CD by Using γ-Cyclodextrin Glycosyltransferase and Isoamylase Simultaneously The method for producing γ-CD by using γ-cyclodextrin glycosyltransferase and isoamylase simultaneously is as follows:
1) The starch was suspended in water to a final concentration of 5-20% and heated to 60-90° C. for about 5-15 min under constantly stirring.
2) 10-100 U γ-CGTase (A223K) and 10-100 U isoamylase per gram of starch were added to the starch slurry after the suspension was cooled down to 40-60° C. and the pH was adjusted to 7.0-8.0. After that, 5% (w/v) cyclododecanone (complexant) was added and the slurry was kept for 6-12 h.
3) When the catalytic reaction was over, the mixture was firstly heated in a boiling water bath for five minutes to inactivate the enzymes and was then filtered directly. The filtered cake was washed with water for 2-3 times. The filtered cake which contained starch and complex formed by cyclododecanone and γ-CD was collected and dissolved in water.
4) The cyclododecanone was removed by azeotropic distillation, and then the complexant-free aqueous solution containing free γ-CD was filtered by Buchner funnel to get rid of insoluble starch. The γ-CD solution was concentrated with a rotary evaporator and then crystallized into pure γ-CD at a low temperature.
5) The γ-CDs were analyzed by HPLC. The supernatant of complexant-free aqueous solution was obtained after centrifugation at 8000 rpm for 15 min. 0.45 μL α-amylase was added to the supernatant. One hour later, the supernatant was filtered through a 0.45 μm filter (Whatman) ahead of being injected into HPLC system (Waters 600) for analysis. Then, 10 μL filtrate was used for analysis and the concentration of γ-CD was determined through HPLC by using a ZORBAX $NH_2$ column (4.6 mm×150 mm) at 40° C. The mobile phase consisted of 75% acetonitrile and 25% water with a flow rate of 1 mL/min. The eluted was detected by a RI detector (Waters2410).

It was found that the γ-CD and β-CD yield was 65.4% and 4.6% respectively, and the conversion rate of starch was 70%.

Example 3

Production of γ-CD by Firstly Using Isoamylase and then γ-Cyclodextrin Glycosyltransferase The method for producing γ-CD by using isoamylase firstly and then γ-cyclodextrin glycosyltransferase is as follows:
1) Example 2, step 1).
2) 10-100 U isoamylase per gram of starch were added to the starch slurry after the suspension was cooled down to 40-60° C. and the pH was adjusted to 7.0-8.0. The reaction was kept for 2-6 hours. Afterwards, 10-100 U γ-CGTase (A223K) and 5% (w/v) cyclododecanone were added and the slurry was kept for 4-10 hours.
3) Example 2, step 3).
4) Example 2, step 4).
5) Example 2, step 5).

It was found that the γ-CD and β-CD yield was 64.3% and 4.5% respectively, and the conversion rate of starch was 68.8%.

Example 4

Production of γ-CD by Utilizing γ-Cyclodextrin Glycosyltransferase Firstly and Then Isoamylase The method for producing γ-CD by utilizing isoamylase firstly and then γ-cyclodextrin glycosyltransferase is as follows:
1) Example 2, step 1).
2) 10-100 U γ-CGTase (A223K) per gram of starch and 5% (w/v) cyclododecanone were added to the starch slurry after the suspension was cooled down to 40-60° C. and the pH was adjusted to 7.0-8.0. The reaction was kept for 2-6 h. Afterwards, 10-100 U isoamylase per gram of starch was added and the slurry was kept for 4-10 h.
3) Example 2, step 3).
4) Example 2, step 4).
5) Example 2, step 5).

It was found that the γ-CD and β-CD yield was 65.6% and 4.1% respectively, and the conversion rate of starch was 69.7%.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

REFERENCES

Nakagawa Y, Takada M, Ogawa K, Hatada Y, Horikoshi K. "Site-directed mutations in Alanine 223 and Glycine 255 in the acceptor site of gamma-Cyclodextrin glucanotransferase from Alkalophilic *Bacillus clarkii* 7364 affect cyclodextrin production." *J. Biochem.* 2006 140(3):329-36.

Pishtiyski, I. and B. Zhekova (2006). "Effect of different substrates and their preliminary treatment on cyclodextrin production." *World Journal of Microbiology and Biotechnology* 22(2): 109-114.

Rendleman, J. A., Jr. (1997). "Enhancement of cyclodextrin production through use of debranching enzymes." *Biotechnology and applied biochemistry* 26(1): 51-61.

What is claimed is:
1. A method for producing γ-CD (cyclodextrin) with isoamylase and γ-CGTase (A223K) (cyclodextrin glycosyltransferase) simultaneously, comprising the steps of:
   a) suspending starch in water to a final concentration of 5-20% and heating to 60-90° C. for about 5-15 min under constant stirring to make a starch slurry;
   b) cooling down the starch slurry to 40-60° C. and adjusting the pH to 7.0-8.0;
   c) adding simultaneously 10-100 U γ-CGTase (A223K) and 10-100 U isoamylase per gram of starch to the starch slurry to make a reaction mixture;

d) adding 5% (w/v) organic complexing agent to the reaction mixture and incubating at 40-60° C. for 6-12 hours; and
e) removing the organic complexing agent and obtaining pure γ-CD by crystallization.

2. The method of claim 1, wherein the method of removing the organic complexing agent comprises the steps of:
   a) heating the reaction mixture to inactivate isoamylase and γ-CGTase (A223K) and filtering the reaction mixture to obtain a filtered cake, which contains starch and a complex formed by the organic complexing agent and γ-CD;
   b) washing the filtered cake with water for 2-3 times;
   c) collecting the filtered cake and dissolving the filtered cake with water;
   d) removing the organic complexing agent by azeotropic distillation and removing insoluble starch by filtration to obtain a γ-CD-containing aqueous solution;
   e) concentrating the γ-CD-containing aqueous solution with a rotary evaporator and generating pure γ-CD by crystallization at a low temperature.

3. The method of claim 1, wherein the organic complexing agent is cyclododecanone.

4. The method of claim 2, wherein the organic complexing agent is cyclododecanone.

* * * * *